US009734600B2

(12) United States Patent
Berker et al.

(10) Patent No.: US 9,734,600 B2
(45) Date of Patent: Aug. 15, 2017

(54) ATTENUATION MAP WITH SCATTERED COINCIDENCES IN POSITRON EMISSION TOMOGRAPHY

(71) Applicant: KONINKLIJKE PHILIPS N.V., Eindhoven (NL)

(72) Inventors: Yannick Berker, Witten (DE); Volkmar Schulz, Wuerselen (DE)

(73) Assignee: KONINKLLIJKE PHILIPS N.V., Eindhoven (NL)

( * ) Notice: Subject to any disclaimer, the term of this patent is extended or adjusted under 35 U.S.C. 154(b) by 290 days.

(21) Appl. No.: 14/396,398

(22) PCT Filed: Apr. 23, 2013

(86) PCT No.: PCT/IB2013/053181
§ 371 (c)(1),
(2) Date: Oct. 23, 2014

(87) PCT Pub. No.: WO2013/164731
PCT Pub. Date: Nov. 7, 2013

(65) Prior Publication Data
US 2015/0098640 A1 Apr. 9, 2015

Related U.S. Application Data

(60) Provisional application No. 61/642,730, filed on May 4, 2012, provisional application No. 61/661,455, filed on Jun. 19, 2012.

(51) Int. Cl.
G06K 9/00 (2006.01)
G06T 11/00 (2006.01)
(Continued)

(52) U.S. Cl.
CPC ............ *G06T 11/005* (2013.01); *A61B 6/037* (2013.01); *A61B 6/5205* (2013.01);
(Continued)

(58) Field of Classification Search
None
See application file for complete search history.

(56) References Cited

U.S. PATENT DOCUMENTS

2010/0021034 A1   1/2010   Lenglet et al.
2010/0116994 A1   5/2010   Wollenweber et al.
(Continued)

FOREIGN PATENT DOCUMENTS

EP        1006370 A2      6/2000

OTHER PUBLICATIONS

Watson, Extension of Single Scatter Simulation to Scatter Correction of Time-of-Flight PET, Oct. 2007, IEEE Transactions on Nuclear Science, vol. 54, No. 5, p. 1679-1686.*
(Continued)

*Primary Examiner* — Manuchehr Rahmjoo

(57) ABSTRACT

An imaging system (36) includes a Positron Emission Tomography (PET) scanner (38) and one or more processors (52). The Positron Emission Tomography (PET) scanner (38) which generates event data including true coincident events and scatter events, the event data includes each end point of a line of response (LOR) and an energy of each end point. The one or more processors (52) are programmed to generate (72) a plurality of activity map and attenuation map pairs based on the true coincident events, and select (76) an activity map and an attenuation map from the plurality of activity and attenuation map pairs based on the scattered events.

20 Claims, 4 Drawing Sheets

Figure 1:
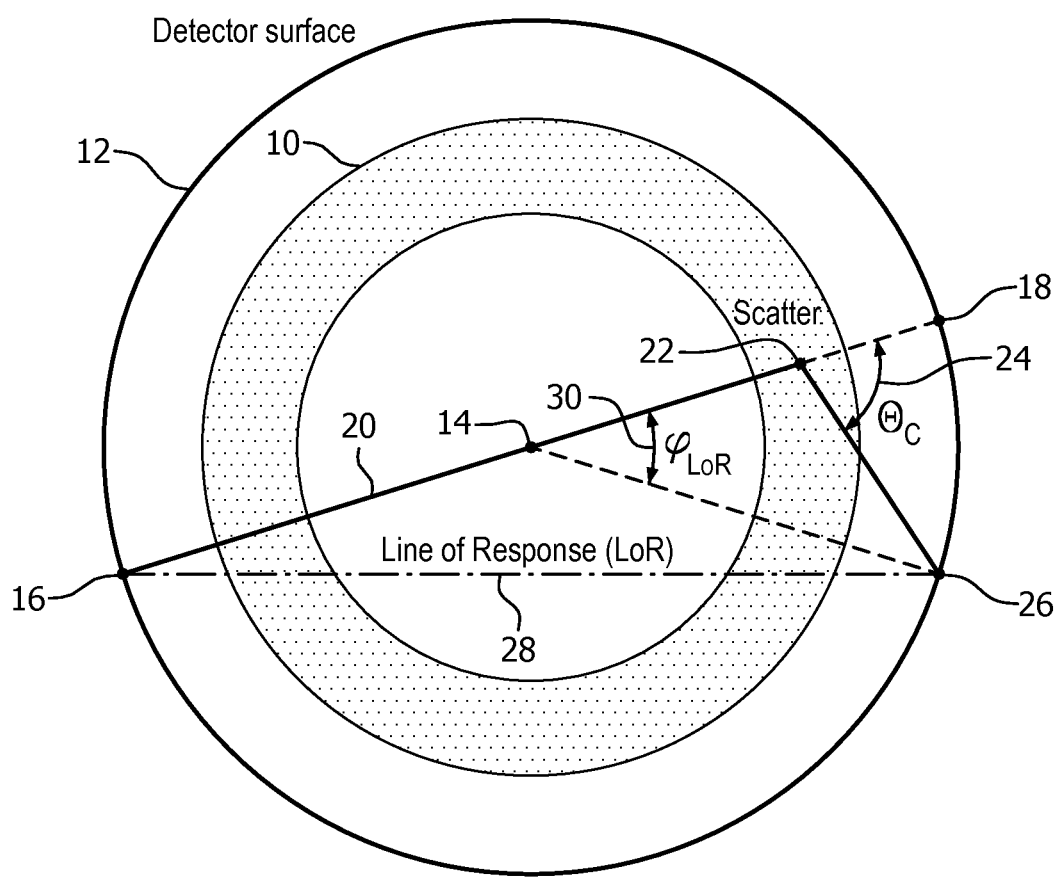

(51) Int. Cl.
    A61B 6/03    (2006.01)
    A61B 6/00    (2006.01)
    G01T 1/164   (2006.01)
    G01T 1/161   (2006.01)
(52) U.S. Cl.
    CPC ............ *A61B 6/5258* (2013.01); *G01T 1/161* (2013.01); *G01T 1/1647* (2013.01)

(56) References Cited

U.S. PATENT DOCUMENTS

| | | | | |
|---|---|---|---|---|
| 2010/0204563 | A1* | 8/2010 | Stodilka | G01R 33/481 600/411 |
| 2011/0015904 | A1* | 1/2011 | Fenchel | A61B 6/037 703/2 |
| 2011/0103669 | A1 | 5/2011 | Michel et al. | |
| 2012/0049053 | A1 | 3/2012 | Olivier et al. | |
| 2014/0376701 | A1* | 12/2014 | Kopperdahl | A61B 6/582 378/207 |

OTHER PUBLICATIONS

Bronnikov, A. V.; Reconstruction of Attenuation Map Using Discrete Consistency Conditions; 2000; IEEE Trans. on Medical Imaging; 19(5)451-462.

Cade, S. C., et al.; Attenuation map estimation without transmission scanning using measured scatter data; 2011; IEEE Nuclear Science & Medical Imaging; 2657-2663.

Conti, M., et al.; Simultaneous reconstruction of scatter and unscattered PET coincidences using TOF and energy information; 2011; IEEE Nuclear Science & Medical Imaging; 2332-2337.

Defrise, M., et al.; Time-of-Flight PET data determine the attenuation sinogram up to a constant; 2012; Phys. Med. Biol.; 1-18.

Natterer, F.; Computerized Tomography with Unknown Sources; 1983; SIAM J. Appl. Math.; 43(5)1201-1202.

Nuyts, J., et al.; Simultaneous Maximum A Posteriori Reconstruction of Attenuation and Activity Distributions from Emission Sinograms; 1999; IEEE Trans. on Medical Imaging; 18(5)393-403.

Rezaei, A.; Simultaneous Reconstruction of Activity and Attenuation in Time-of-Flight PET; 2011; IEEE Nuclear Science & Medical Imaging; 2375-2382.

Salomon, A., et al.; Simultaneous Reconstruction of Activity and Attenuation for PET/MR; 2011; IEEE Trans. on Medical Imaging; 30(3)804-813.

Vandervoort, E., et al.; An Analytical Scatter correction for Singles-Mode Transmission Data in PET; 2008; IEEE Trans. on Medical Imaging; 27(3)402-412.

Welch, A., et al.; Attenuation Correction in PET Using Consistency Information; 1998; IEEE Trans. on Nuclear Science; 45(6)3134-3141.

* cited by examiner

ATTENUATION MAP WITH SCATTERED COINCIDENCES IN POSITRON EMISSION TOMOGRAPHY

CROSS REFERENCE TO RELATED APPLICATIONS

This application is a national filing of PCT application Serial No. PCT/IB2013/053181, filed Apr. 23, 2013, published as WO 2013/164731 A1 on Nov. 7, 2013, which claims the benefit of U.S. provisional application Ser. No. 61/642,730 filed May 4, 2012 and U.S. provisional application Ser. No. 61/661,455, filed Jun. 19, 2012, both of which are incorporated herein by reference.

The following relates generally to nuclear medicine imaging. It finds particular application in conjunction with estimating attenuation in Positron Emission Tomography, and will be described with particular reference thereto. However, it will be understood that it also finds application in other usage scenarios and is not necessarily limited to the aforementioned application.

In Positron Emission Tomography (PET), a radiopharmaceutical is administered to a subject. As the radiopharmaceutical emits positrons in decay, the positrons strike nearby electrons and in an annihilation event emit two photons of energy in opposite directions. The photons are approximately 511 keV in energy. The emitted photons are recorded by detectors in a circumferential arrangement. True coincident events are measured at nearly the same time and are used to determine where the photons were emitted. The path for emission of true coincident events is called a line of response (LOR). With time-of-flight (TOF) PET the time of each strike of a photon can be used to compute the distance along the LOR for a better estimate of the point source of the emitted photon. The amount or quantity of photons emitted by the decaying radiopharmaceutical is called the activity.

Radiopharmaceuticals are administered to identify locations of a particular metabolic activity such as a cancerous growth. The radiopharmaceutical concentrates in the region of the targeted metabolic activity. As the radiopharmaceutical decays in the targeted region and photons are emitted, the activity of the targeted region is measured based on the emitted photons, and an image is reconstructed by the PET system. The reconstructed image shows the region of the particular metabolic activity contrasted by the measured activity of the radiopharmaceutical.

However, some emitted photons are absorbed. Attenuation includes photons which are absorbed based on the material or matter through which the photons must travel before they are detected. Photons are either absorbed or not. Material which is denser has greater attenuation and absorbs more photons. In measuring photon strikes at a detector, both the activity and the attenuation are key variables. A large amount of activity with great attenuation can appear similar in measurement to smaller activity with less attenuation.

Attenuation correction is addressed in some systems through the use of X-ray Computed Tomography (CT). Some systems are combination or hybrid systems. CT systems are useful for attenuation correction because the intensity of a CT image correlates strongly with attenuation. For example, bones are very bright in intensity and dense. Bones have greater attenuation. However, there are standalone PET systems and there is greater interest in combination of Magnetic Resonance (MR) imaging and PET imaging, which do not include CT.

Attenuation correction with standalone PET systems includes such algorithms as Maximum Likelihood Expectation Maximization (MLEM) and Maximum-Likelihood Reconstruction of Activity and Attenuation (MLAA). These techniques use true coincidences of measured photon emissions, and iterations of combinations of activity and attenuation to try to converge on a unique solution which estimates both activity and attenuation. These techniques are sometimes limited or need additional outside information. For example, where there is circumferential symmetry of the attenuation, such as the head, the true coincident events do not provide information to discern the difference between activity and attenuation.

Some emitted photons are deflected or Compton scattered. As photons are scattered, the photons lose energy based on the angle of deflection. In typical PET systems, scattered photons are simply excluded. For example, a strike of a measured 511 keV photon establishes a first photon. A nearly simultaneous strike of a second photon of 450 keV indicates a corresponding, but scattered photon. In most PET, the two events are excluded from further processing. In some PET systems, if the energy is close to the theoretical 511 keV, there is uncertainty in the true trajectory of the LOR. If the event is close enough to 511 keV, the LOR is used in the reconstruction to improve sensitivity. Other, more scattered photon events with energies further from 511 keV are discarded.

The following discloses a new and improved attenuation map based on scattered coincidences which addresses the above referenced issues, and others.

In accordance with one aspect, an imaging system includes a Positron Emission Tomography (PET) scanner, and one or more processors. The PET scanner generates event data including true coincident events and scatter events and the event data includes each end point of a line of response (LOR) and an energy of each end point. The one or more processors are programmed to generate a plurality of activity map and attenuation map pairs based on the true coincident events, and select an activity map and an attenuation map from the plurality of activity and attenuation map pairs based on the scattered events.

In accordance with another aspect, a method of imaging includes receiving event data which includes true coincident events and scatter events, and the event data includes each end point of a line of response (LOR) and an energy of each end point. A plurality of activity map and attenuation map pairs based on the true coincident events are generated. An activity map and an attenuation map are selected from the plurality of activity and attenuation map pairs based on the scattered events.

In accordance with another aspect, an image processing system includes a list of positron emission tomography (PET) event data, and one or more processors. The list of PET event data includes a plurality of unscattered coincident events and scattered coincident events, and the event data includes an end point and an energy of each event. The one or more processors are programmed to generate an attenuation map from the scatter events. The one or more processors are further programmed to reconstruct an image based on the coincident events and the generated attenuation map.

One advantage resides in estimated attenuation maps using PET information.

Another advantage includes the ease of using existing PET systems.

Another advantage resides in using information which can be collected with existing hardware.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a symmetric imaging shell in a PET scanner.

Figure 2:
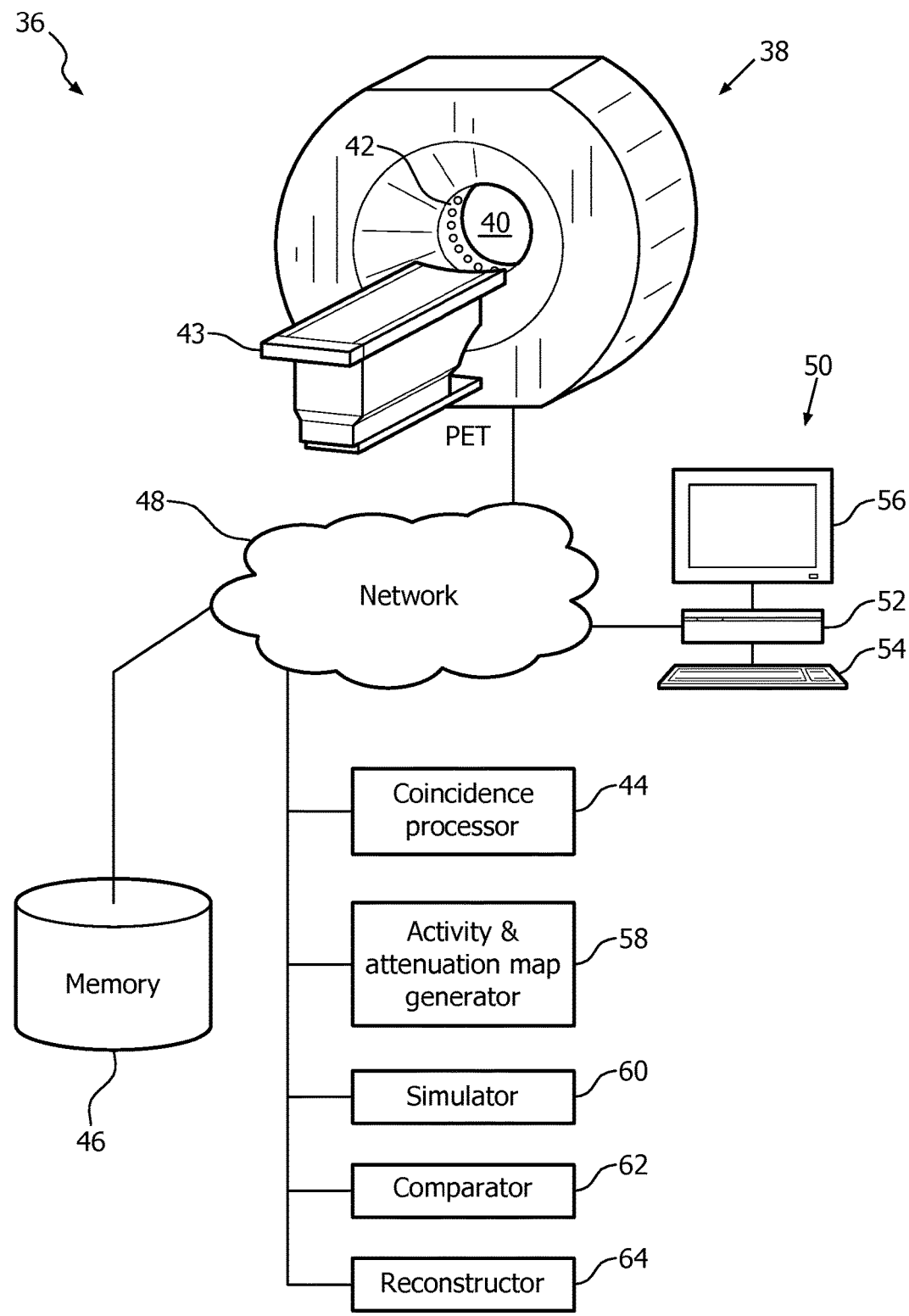

FIG. 2 schematically illustrates an embodiment of the PET system which estimates attenuation based on scattered events.

Figure 3:
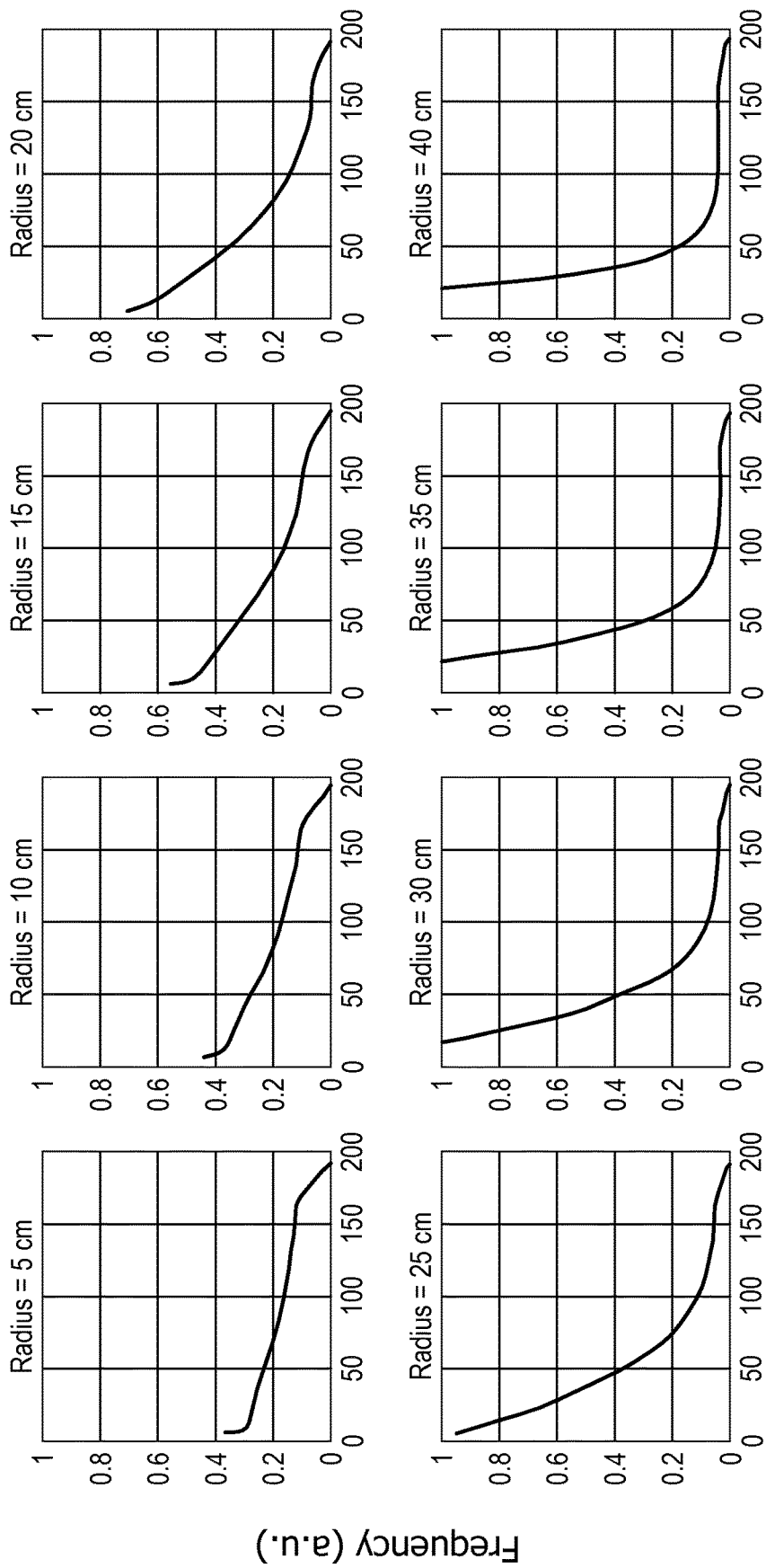

FIG. 3 graphically illustrates distributions of scattered events with various symmetric shell embodiments.

Figure 4:
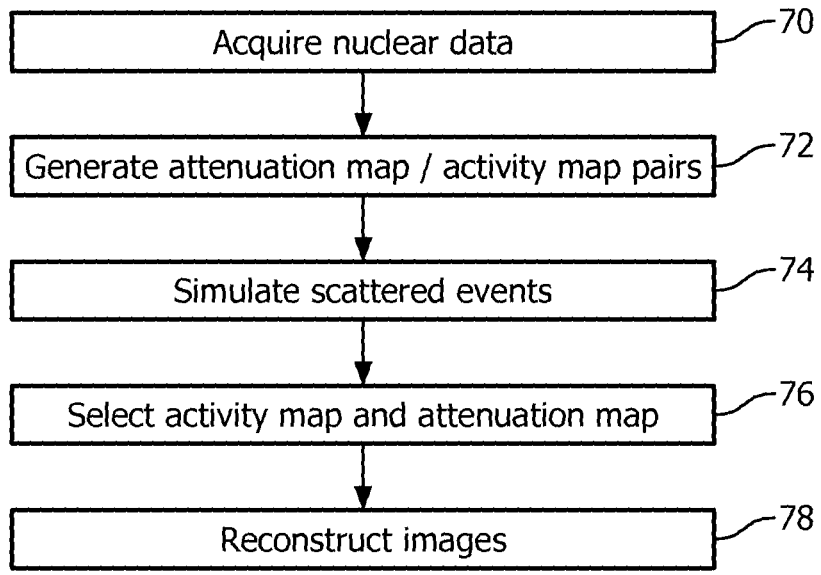

FIG. 4 flowcharts one method of using an embodiment estimating attenuation based on scattered events.

Figure 5:
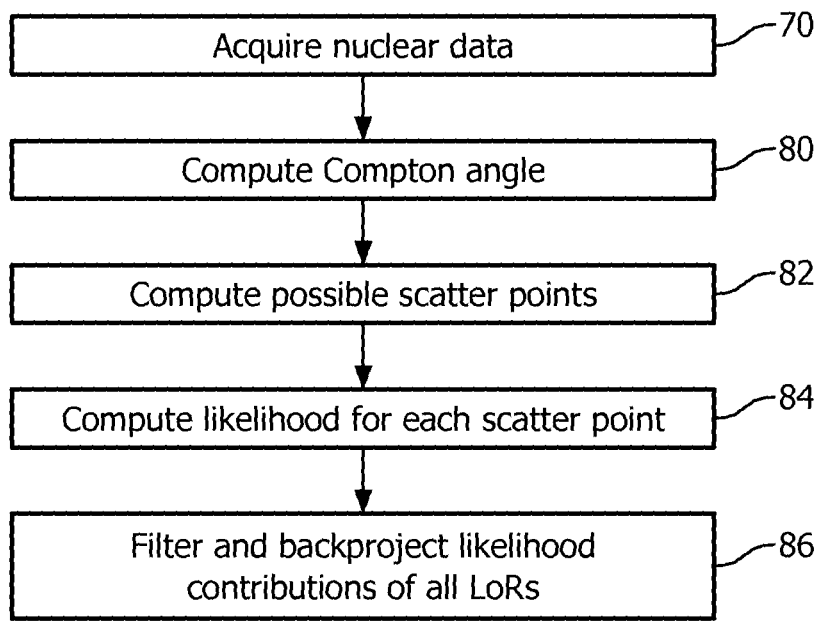

FIG. 5 flowcharts one method of using an embodiment generating an attenuation map based on scatter only.

With reference to FIG. 1, an embodiment of a symmetric imaging shell 10 in a PET scanner is schematically illustrated. The shell is placed within the detector surface 12 or in the bore of the PET scanner. Centered within the imaging shell 10 is a point source of a radiopharmaceutical 14. As the radiopharmaceutical emits radiation and the radiation strikes material, an annihilation event occurs. The annihilation event causes two gamma photons of 511 keV energy to be emitted in opposite directions. True coincident events are events where the photons travel unimpeded in opposite directions to the detector surface 12 and establish two end points 16, 18. The line of travel 20 for true events is the line between the end points.

With a shell present of a uniform density and thickness, attenuation and scatter occurs. Some photons are absorbed which decreases the number of strikes to the detectors or the number of record events. The activity is the amount of decays measured as by the photons emitted by the source. The attenuation acts to reduce the recorded amount of events because photons do not reach the detector. For a symmetric imaging shell, the recorded photon flux is radially symmetric and proportional to $A \cdot e^{-\mu \cdot d}$ where A is the activity at the point source, $\mu$ is the linear attenuation coefficient, and d is the thickness of the shell. Due to dead time effects, the true coincidence rate changes slightly with the shell radius, e.g. monotonically and significantly above the level of statistical fluctuations. Because this term does not involve the radius of the shell, the shell can be placed anywhere within the bore of the PET system, and with only true (511 keV) events certain pairs of activity and attenuation cannot be distinguished. As an example, for any inside diameter of the shell, and an arbitrary scaling parameter $\alpha>0$, the distributions of $(A, \mu, d)$ and $(A, \mu^*\alpha, d/\alpha)$ cannot be distinguished. In more general terms, all attenuation distributions yielding the same attenuation-path product $\int\mu(s)ds$ as $(A, \mu, d)$ along all measured LORs where s is a parameter along the LOR, are not discernible. This situation is called attenuation self-cross-talk. Furthermore, $(A, \mu, d)$ and $(A^*e^{((\alpha-1)^*\mu^*d)}, \mu^*\alpha, d)$ are also not discernable. The latter is called cross-talk between activity and attenuation and has been appreciated and observed in clinical cases and solved to a constant unknown offset in either activity or attenuation. Attenuation self-cross-talk and cross-talk between activity and attenuation are resolved using the amount, the distribution, and the properties of scattered events.

A scattered event 22 occurs when a photon strikes a material such as the shell and is deflected at an angle 24 with a loss of energy. Instead of striking at an end point along the original emission path 18, the photon is deflected and strikes at a different end point 26. The recorded end points 16, 26 form a line of response (LOR) 28. An LOR angle 30 is the computed as the angle between the original line of travel 20 and the recorded end point. The event is known as scattered because the energy recorded at the end point 26 of the deflected photon is less than the 511 keV, such as 508 keV or lower.

FIG. 2 schematically illustrates an embodiment of a PET system 36 which estimates attenuation based on scattered events. The system includes a PET scanner 38. The PET scanner 38 has a toroid shaped opening 40 or bore which receives the subject. The subject is supported by a subject support 43 such as a bed or couch. The radiopharmaceutical is administered to the subject, and the subject is placed in the opening 40 or bore of the scanner. The opening or bore is lined with detectors 42 which detect emitted photons from the subject. The PET scanner includes a coincidence processor 44. As each photon strikes a detector, the coincidence processor 44 records the time, energy, and location of the strike in a memory 46. The recorded list of strikes is stored in memory, e.g. in a list mode. The coincidence processor can provide time and energy gating or filtering to the memory to identify events scattered and unscattered. Scattered events are included in the memory. For example, including an event with energy between 190 keV and 509 keV paired with another strike of approximately 511 keV will include a scattered LOR. The energy sensitivity or loss due to the detector is adjusted in the gating parameters. Another gating parameter can include the LOR angle such as greater than or equal to 4.2°. The scanner and memory are connected to a network 48 for storage and retrieval of the event data. The storage can include software storage and image storage.

The system includes a workstation 50. The workstation 50 connects to the network 48. The workstation 50 includes an electronic processor or electronic processing device 52, at least one input device 54, and a display 56 which displays maps, images, menus, panels, and user controls. The at least one input device 54 inputs the healthcare practitioner selections. The workstation 50 can include an array of computers, an array processor, a desktop computer(s), a laptop, a tablet, a mobile computing device, a smartphone, and the like. The input device can be a keyboard, a mouse, a microphone, and the like.

An activity and attenuation map generator 58 inputs the event data and generates activity map and attenuation map pairs. The pairs can include similar distributions based on the event data. The activity and attenuation map generator filters the event data for true unscattered coincident pairs to generate the pairs of maps. The algorithm can include MLAA, MLEM, and the like.

In an alternative embodiment, the activity and attenuation map generator 58 generates an attenuation map directly from scatter only. For each LOR, a Compton angle is computed based on the energy of the scattered photon using the Klein-Nishina formula or scatter cross-section database such as XCOM. From the end points of the LOR and the Compton angle, a surface of possible scatter points is computed. To the extent the energy is known, every possible scatter point is situated on a family of circular arcs through the LOR endpoints. With some uncertainty in the energy value, the surface of possible scatter points becomes a volume of possible scatter points. A likelihood of each scatter point is computed from geometrical considerations and other a-priori information. In a backprojection step, the likelihood contributions of all LORs are summed. Each LOR can again be weighted based on the Klein-Nishina formula and geometrical information. An optional filtering can follow such as in filtered backprojection (FBP) approaches to generate the attenuation map. Using non-scattered events as wells as scattered events is also contemplated.

A simulator 60 inputs the plurality of map pairs and simulates distributions of scattered events (simulated list mode data) that could have generated each map pair. The simulated distributions of scattered events are compared with the actual distribution of scattered events from the list mode memory by a comparator 62. The comparator can alternatively decompose the distributions for the constituent components such as by each voxel as a point source. The distributions can be compared with the actual distribution based on a least squares minimization to select the best fit activity and attenuation map pair. The selection of the activity and attenuation map pair based on the scattered event resolves the cross-talk or self-cross-talk between the generated pairs which include similar distributions.

A reconstruction unit 64 reconstructs one or more images based on the selected attenuation map and the event data. In the embodiment of direct generation of the attenuation map from scatter only, the generated attenuation map is the selected attenuation map. The event data is filtered to remove scattered events and input the true coincident LORs in the reconstruction. The selected attenuation map provides the attenuation corrections during the reconstruction. Alternatively, the activity map can be reconstructed as the one or more images representing the presence of the radiopharmaceutical or metabolic activity in the subject.

The coincidence processor 44, activity and attenuation map generator 58, simulator 60, comparator 62, and reconstruction unit 64 are suitably embodied by one or more electronic data processing device(s), such as the electronic processor or electronic processing device 52 of the workstation 50, or by a network-based server computer operatively connected with the workstation 50 by the network 48, or so forth. Moreover, the disclosed activity and attenuation map generation and selection techniques are suitably implemented using a non-transitory storage medium storing instructions (e.g., software) readable by an electronic data processing device and executable by the electronic data processing device to perform the disclosed activity and attenuation map generation and selection techniques.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer-readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

FIG. 3 graphically illustrates distributions of scattered events with various symmetric shell embodiments. Each histogram is of scattered event distribution for a shell such as approximately 10 cm uniformly thick with a radius of 5 cm to 40 cm in steps of 5 cm. With true coincident events, the activity and attenuation maps do not distinguish a difference between the shell sizes. However, with scattered events the distribution can be used to determine the shell size or differentiate among a plurality of possible activity and attenuation map pairs.

The difference in the distribution of histograms illustrates how scattered events provide additional information to resolve self-cross-talk. Similar alternative configurations can illustrate how to resolve the cross-talk of activity and attenuation by varying both the activity of the point source and the attenuation such as the path integral along all LORs. The first histogram includes the distribution of scattered events for a small (r=5 cm) shell. The distributions are shown based on the recorded energy level across multiple LOR angles collected for the same acquisition time such as 120 seconds. The small shell shows a broader distribution with a more gradual slope as the LOR angle increases. As the shell size increases the distribution narrows with a steeper slope as the LOR angle increases. Based on the actual distribution of scattered events, the distribution provides the information to resolve the cross-talk and self-cross-talk ambiguities between generated activity and attenuation map pairs based on the true coincident events.

FIG. 4 flowcharts one method of using an embodiment estimating attenuation based on scattered events. In a step 70, event data is acquired. The subject is administered the radiopharmaceutical and positioned in the bore or opening of the scanner on the subject support. As the radiopharmaceutical decays, emits positrons, and the positrons cause annihilation events, photon pairs are emitted. The emitted photons are recorded as strikes by the detectors. As the detectors detect the strikes, the event pairs and the energy of each event are recorded by the coincidence processor in the list mode memory. The coincidence processor includes scattered events and true coincident events in the list mode memory.

The activity and attenuation map generator receives the list mode data from the list mode memory and generates a plurality of the activity map and attenuation map pairs in a step 72. The pairs can be generated using algorithms such as MLAA, MLEM, and the like. The algorithms use the true coincident events filtered from the list mode memory.

In a step 74, a simulator based on the plurality of activity and attenuation map pairs simulates, e.g. a Monte Carlo simulation, one or more distributions of scattered events. If present, time of flight (TOF) can provide additional information which can supplement the information derived from the distribution of scattered events or be used to reduce the quantity of simulations. The simulated distributions of scattered events are compared or fit to the actual distribution of scattered events filtered from the list mode data to select the best fit activity map and the attenuation map in a step 76. The selection process resolves the cross-talk and self-cross-talk problem and provides a convergent solution for the generated activity and attenuation map pairs.

One or more images are reconstructed by the reconstruction unit in a step 78. The reconstruction unit uses the filtered true coincident events and the selected attenuation map to reconstruct one or more images. The images can include 2D projections, 2D slices, or 3D volumes. Alternatively, the reconstruction unit can reconstruct from the activity map of the selected activity and attenuation map pair. The one or more images are displayed on the display 56 of the workstation or another display.

With reference to FIG. 5, in another embodiment an attenuation map is generated based on scatter only. In a step 80, for each LOR, the Compton angle is computed from the scattered photon's energy using the Klein-Nishina formula or scatter cross-section databases such as XCOM. From the end points of the LOR and the Compton angle, a surface of possible scatter points is computed in a step 82. To the extent the energy is known, every possible scatter point is situated on a family of circular arcs through the LOR endpoints. With some uncertainty in the energy value, the surface of possible scatter points becomes a volume of possible of scatter points. A likelihood of each scatter point is computed from geometrical considerations and other a-priori information in a step 84. Each LOR can again be weighted based on the Klein-Nishina formula and geometrical information. In a step 86, filtering and a backprojection are applied to the likelihood distribution for each LOR, such as in filtered backprojection (FBP) approaches, to generate the attenuation map and an image. Using non-scattered events as well as scattered is also contemplated.

Attenuation-corrected image reconstruction from all events can include a standard image reconstruction from trues and photo-peak scatter, including scatter correction and the like, but could also incorporate additional scattered events.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An imaging system, comprising:
a Positron Emission Tomography (PET) scanner which generates event data including true coincident events and scatter events, the event data includes each end point of a line of response (LOR) and an energy of each end point; and
one or more processors programmed to:
generate a plurality of activity map and attenuation map pairs based on the true coincident events; and
select an activity map and an attenuation map from the plurality of activity and attenuation map pairs based on the scattered events.

2. The imaging system according to claim 1, wherein the one or more processors are further programmed to:
reconstruct an image based on the selected activity map.

3. The imaging system according to claim 1, wherein the plurality of activity map and attenuation map pairs include similar distributions.

4. The imaging system according to claim 1, wherein scattered events includes energy between 190 keV and 509 keV and a line or response (LOR) deflection angle greater than or equal to 4.2°.

5. An imaging system comprising:
a Positron Emission Tomography (PET) scanner configured to generate event data including true coincident events and scatter events, the event data including each end point of a line of response (LOR) and an energy of each end point; and
one or more processors programmed to:
generate a plurality of activity map and attenuation map pairs based on the true coincident events;
simulate a distribution of at least the scattered events based on each of the activity and attenuation map pairs; and
select the activity and attenuation map pair based on a comparison between the simulated distribution of scattered events and a recorded distribution of scattered events constructed from the recorded scattered events.

6. The imaging system according to claim 5, wherein the one or more processors are further programmed to:
decompose a distribution of scattered events into attenuation components based on the end point location.

7. The imaging system according to claim 6, wherein the decomposition includes voxels as a point source of activity.

8. The imaging system according to claim 5, wherein the one or more processors are further programmed to:
reconstruct an image based on the true coincident events and the selected attenuation map.

9. The imaging system according to claim 5, wherein the distribution of scattered events includes a computed angle of deflection.

10. The imaging system according to claim 5, wherein the distribution of scattered events includes a frequency of occurrence of an offset of an angle of deflection.

11. A method of imaging, comprising:
receiving event data which includes true coincident events and scatter events, the event data includes each end point of a line of response (LOR) and an energy of each end point;
generating a plurality of activity map and attenuation map pairs based on the true coincident events; and
selecting an activity map and an attenuation map from the plurality of activity and attenuation map pairs based on the scattered events.

12. The method according to claim 11, further including:
simulating a distribution of at least the scattered events based on each of the activity and attenuation map pairs; and
selecting the activity and attenuation map pair based on a comparison between the simulated distribution of scattered events and a recorded distribution scattered events constructed from the recorded scattered events.

13. A non-transitory computer-readable storage medium carrying software which controls one or more electronic data processing devices to perform a method according to claim 12.

14. The method according to claim 11, further including:
decomposing a distribution of scattered events into attenuation components based on the end point location.

15. The method according to claim 11, further including:
reconstructing an image based on the true coincident events and the selected attenuation map.

16. The method according to claim 11, further including:
reconstructing an image based on the selected activity map.

17. The method according to claim 11, wherein the plurality of activity map and attenuation map pairs include similar distributions.

18. The method according to claim 11, wherein a distribution of scattered events includes a computed angle of deflection.

19. An electronic data processing device configured to perform a method according to claim 11.

20. An image processing system, comprising:
a list of positron emission tomography (PET) event data including a plurality of true coincident events and scattered coincident events, the scattered coincident events undergoing an angle of deflection greater than or equal to 4.2°, and the event data including end points and an energy of each event; and
one or more processors programmed to:
compute the angle of deflection for each scattered event;
simulate a distribution of the scattered events using the computed angles of deflection;
decompose the distribution of the scattered events into an attenuation map; and
reconstruct the true coincident events into an image based on using the attenuation map to correct for attenuation.

* * * * *